(12) United States Patent
Lingelbach et al.

(10) Patent No.: US 11,869,646 B1
(45) Date of Patent: Jan. 9, 2024

(54) MEDICATION VALIDATION SYSTEM AND RELATED METHODS

(71) Applicant: INMAR Rx SOLUTIONS, INC., Ft. Worth, TX (US)

(72) Inventors: Matthew Lingelbach, Clemmons, NC (US); Melissa Bube, High Point, NC (US); Vlad A. Catlan, Winston-Salem, NC (US); Marko Milojevic, Jamestown, NC (US); Jared O. Santibanez, Forney, TX (US)

(73) Assignee: INMAR RX SOLUTIONS, INC., Ft. Worth, TX (US)

( * ) Notice: Subject to any disclaimer, the term of this patent is extended or adjusted under 35 U.S.C. 154(b) by 226 days.

(21) Appl. No.: 17/327,196

(22) Filed: May 21, 2021

(51) Int. Cl.
   *G16H 20/13* (2018.01)
   *G06Q 10/087* (2023.01)
   *G16H 70/40* (2018.01)

(52) U.S. Cl.
   CPC ........... *G16H 20/13* (2018.01); *G06Q 10/087* (2013.01); *G16H 70/40* (2018.01)

(58) Field of Classification Search
   CPC ..... G07F 17/0092; G16H 20/13; G16H 40/20
   See application file for complete search history.

(56) References Cited

U.S. PATENT DOCUMENTS

| 7,783,383 | B2 | 8/2010 | Eliuk et al. | |
|---|---|---|---|---|
| 2006/0054682 | A1* | 3/2006 | de la Huerga | G16H 20/10 |
| | | | | 235/375 |
| 2007/0043469 | A1* | 2/2007 | Draper | G16H 20/13 |
| | | | | 700/231 |
| 2008/0056556 | A1* | 3/2008 | Eller | G07F 17/0092 |
| | | | | 382/142 |
| 2017/0246083 | A1 | 8/2017 | Amano et al. | |
| 2018/0260665 | A1 | 9/2018 | Zhang et al. | |
| 2019/0139639 | A1* | 5/2019 | Woodyear | G16H 20/10 |

OTHER PUBLICATIONS

McCracken et al., U.S. Appl. No. 16/395,343, filed Apr. 26. 2019.

* cited by examiner

*Primary Examiner* — Timothy R Waggoner
(74) *Attorney, Agent, or Firm* — ALLEN, DYER, DOPPELT, + GILCHRIST, P.A.

(57) ABSTRACT

A medication validation system may include a camera to capture an image of a medication container that may have physical container characteristics associated therewith and a computer-readable indicia affixed thereon. A validation server may obtain stored medication physical container characteristics and associated stored computer-readable indicia, and obtain image data associated with the image from the camera. The image data may be representative of the physical container characteristics of the medication container. The validation server may determine the physical container characteristics of the medication container from the obtained image data, and determine the computer-readable indicia from the obtained image data. The validation server may also determine whether the medication container is mislabeled based upon an attempted matching of both of the stored and obtained medication container characteristics and the stored and obtained computer-readable indicia indicative that the medication container is mislabeled, and communicate a notification that the medication container is mislabeled.

13 Claims, 14 Drawing Sheets

MEDICATION VALIDATION SYSTEM AND RELATED METHODS

TECHNICAL FIELD

The present invention relates to the field of medicine, and more particularly, to medication inventory systems and related methods.

BACKGROUND

Medications, including controlled substances, medical devices, and/or medical tools may be relatively important for treatment of a patient. Thus, it may be desirable to maintain medications in a relatively orderly and predictable fashion to reduce the amount of time it takes to access these medications, particularly in a time sensitive situation.

A medication tray is often used to provide a specific selection and quantity of medications for a particular medical use case, physician preference, and/or location. A given health care facility hospital may have multiple variations of medication trays in use, each varying in type, amount, and/or placement of medications within the medication tray. Multiple medication trays may be used within a crash cart, which is a wheeled cart for dispensing of medication (e.g., in an emergency). Consequently, health care facility pharmacies may process and manage a relatively large quantity of medication trays used throughout a facility.

Accordingly, the medication trays are typically managed. Contents of the medication trays may be replenished and verified, for example, between uses. The verification may be performed manually and include inspection for recalled, expired, and misplaced medications.

U.S. Patent Application Publication No. 2017/0246083 to Amano et al. is directed to a medicine sorting apparatus. More particularly, Amano et al. discloses a medicine sorting apparatus that includes an identifying part, e.g., based upon a camera, which can identify a direction, a posture and characteristics such as a shape, a size, a type and an expiration date of a medicine, and a storing part for storing the medicine so that the medicine can be taken from the storing part. A determination processing part can determine whether or not the medicine is a target to be treated based on the characteristics of the medicine identified by the identifying part.

U.S. Patent Application Publication No. 2018/026065 to Zhang et al. is directed to a deep learning system for recognizing pills in images. More particularly, the system and method use deep learning, including convolutional neural networks, to identify subject objects in unconstrained user images such as unknown pills. An image of, e.g., a pill, may be captured and subsequently processed using deep learning models to identify the pill. The deep learning models may be optimized to have a small footprint (in terms of computational and memory resources) suitable for a resource-limited device such as a smartphone while retaining a high object recognition accuracy. Each such model may also be run on modified versions of the unconstrained image, for example on color, greyscale, and gradient images, to focus the models on different distinguishing features of the object.

SUMMARY

A medication validation system may include a camera configured to capture an image of a medication container. The medication container may have physical container characteristics associated therewith and a computer-readable indicia affixed thereon. The medication validation system may also include a validation server configured to obtain a plurality of stored medication physical container characteristics and associated stored computer-readable indicia, and obtain image data associated with the image from the camera. The image data may be representative of the physical container characteristics of the medication container. The validation server may be configured to determine the physical container characteristics of the medication container from the obtained image data, and determine the computer-readable indicia from the obtained image data. The validation server may also be configured to determine whether the medication container is mislabeled based upon an attempted matching of both of the stored and obtained medication container characteristics and the stored and obtained computer-readable indicia indicative that the medication container is mislabeled, and communicate a notification that the medication container is mislabeled.

The system may include a medication tray that includes a plurality of partitions defining a plurality of compartments. One of the plurality of compartments may be for storing the medication container, for example.

The system may include a mobile wireless communications device that includes a housing and wireless communications circuitry carried by the housing. The camera may be carried by the housing, for example. The validation server may be configured to communicate the notification to the mobile wireless communications device, for example.

The validation server may be configured to communicate the notification to a remote device. The validation server may be configured to update the plurality of stored medication physical container characteristics and associated stored computer-readable indicia based upon a match within respective thresholds of both of the stored and obtained medication container characteristics and the stored and obtained computer-readable indicia indicative that the medication container is correctly labeled, for example.

The physical container characteristics may include at least one of container shape, a container size, and a container color, for example. The computer-readable indicia may include a barcode.

The system may include a label affixed to the medication container, and the label may have the computer-readable indicia printed thereon. The label may have label text printed thereon, for example.

A method aspect is directed to a method of validating a medication. The method may include using a validation server to obtain a plurality of stored medication physical container characteristics and associated stored computer-readable indicia, and obtain image data associated with an image of a medication container from a camera. The image data may be representative of physical container characteristics of the medication container, and the medication container may have a computer-readable indicia affixed thereon. The method may include using the validation server to determine the physical container characteristics of the medication container from the obtained image data, and determine the computer-readable indicia from the obtained image data. The method may further include using the validation server to determine whether the medication container is mislabeled based upon an attempted matching of both of the stored and obtained medication container characteristics and the stored and obtained computer-readable indicia indicative that the medication container is mislabeled, and communicate a notification that the medication container is mislabeled.

A computer readable medium aspect is directed to a non-transitory computer readable medium for validating a medication. The non-transitory computer readable medium includes computer executable instructions that when executed by a processor of a validation server cause the processor to perform operations. The operations may include obtaining a plurality of stored medication physical container characteristics and associated stored computer-readable indicia, and obtaining image data associated with an image of a medication container from a camera. The image data may be representative of physical container characteristics of the medication container. The medication container may have a computer-readable indicia affixed thereon. The operations may include determining the physical container characteristics of the medication container from the obtained image data, and determining the computer-readable indicia from the obtained image data. The operations may also include determining whether the medication container is mislabeled based upon an attempted matching of both of the stored and obtained medication container characteristics and the stored and obtained computer-readable indicia indicative that the medication container is mislabeled and communicating a notification that the medication container is mislabeled.

DETAILED DESCRIPTION

The present invention will now be described more fully hereinafter with reference to the accompanying drawings, in which preferred embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like numbers refer to like elements throughout, and prime notation is used to indicate similar elements in alternative embodiments.

Figure 1:
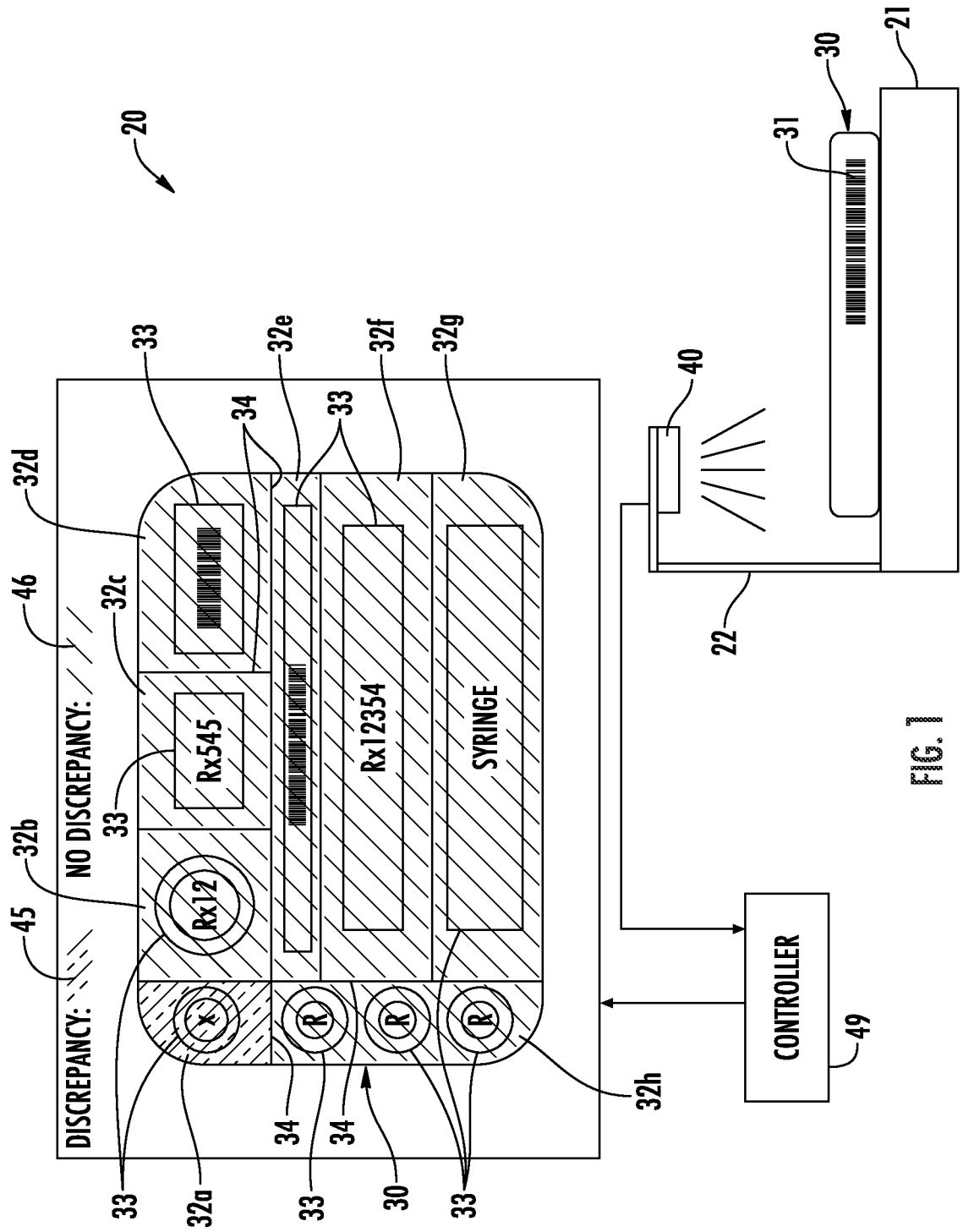
FIG. 1 is a schematic diagram of a medication inventory system according to an embodiment.
Figure 2:
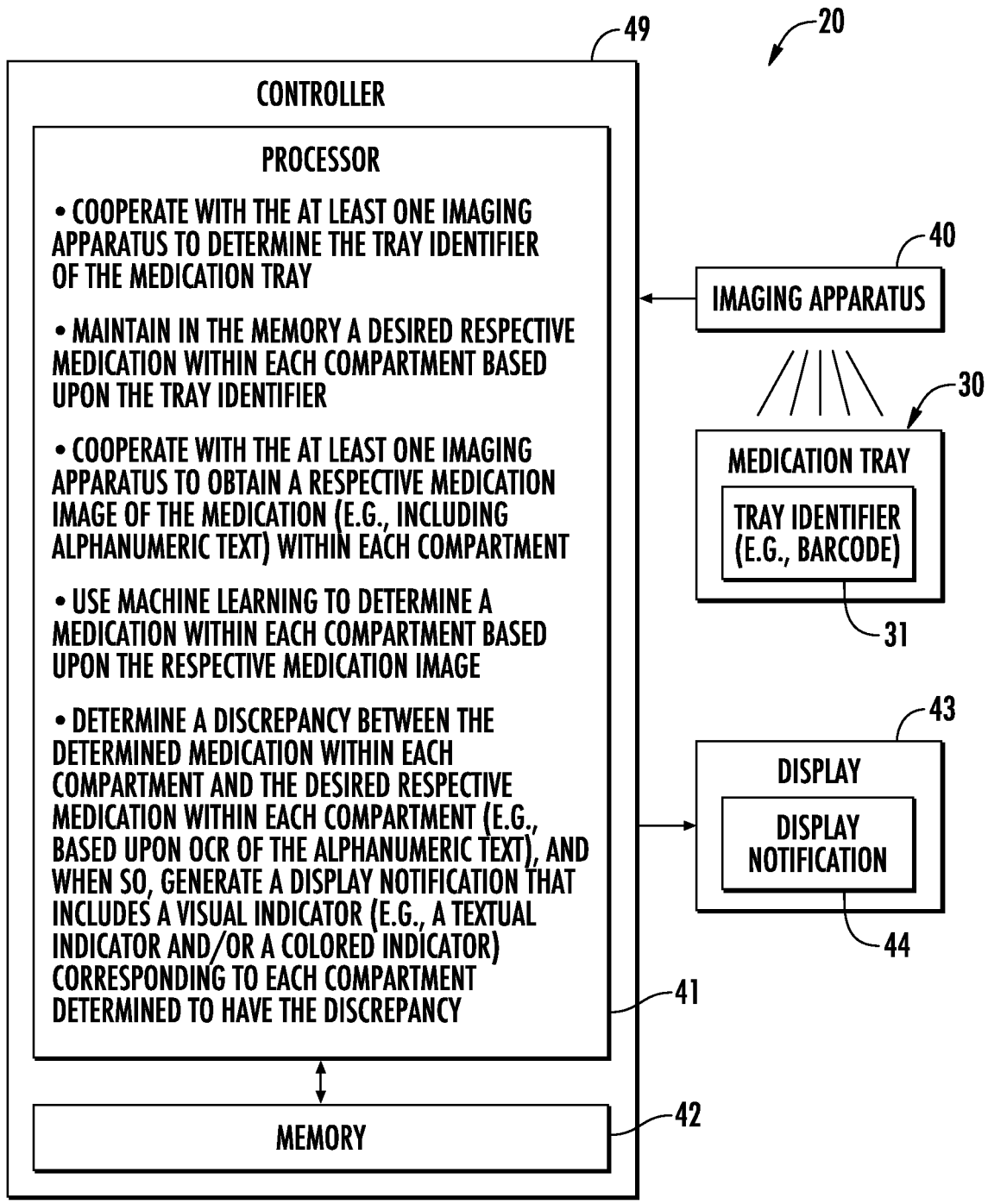
FIG. 2 is a schematic block diagram of the medication inventory system of FIG. 1.

Referring initially to FIGS. 1 and 2, a medication inventory system 20 illustratively includes a medication tray 30. The medication tray 30 includes partitions 34 that define compartments 32a-32h. Each compartment may store a medication 33, multiple medications, a medical or medicated device, a medication container that includes individual medications therein, or other item or substance used for medical treatment. For example, the medication tray 30 may be part of a crash cart, as will be appreciated by those skilled in the art. Of course, the medication tray 30 may be used in other medical environments, for example, an examination room, emergency room, treatment room, operating room, etc.

The medication tray 30 has a tray identifier 31 associated therewith. The tray identifier 31 may be in the form of a barcode, for example, that may be printed or applied (e.g., via an adhesive label) on the medication tray 30. The tray identifier 31 may be in the form of another type of identifier, for example, a quick-response (QR) code, alphanumeric characters, or other optically recognizable and unique code.

The medication inventory system 20 includes a support table 21, for example, in the form of a flat surface, to carry the medication tray 30. In other words, the medication tray 30 may be placed flat on the support table 21, for example, for imaging, as will be described in further detail below. In some embodiments, a support table 21 may not be used.

An arm 22 is coupled to the support table 21 and extends above the support table. The medication inventory system 20 also includes an imaging apparatus 40 carried by the arm 22 and spaced above the support table 21. The arm 22 may be articulating or adjustable (e.g., in height) to accommodate different sized medication trays 30 on the support table 21 and so that the imaging apparatus 40 includes the entire medication tray within its field of view. In some embodiments, the arm 22 may be a fixed arm so that the imaging apparatus 40 is fixedly spaced above the table 21.

The imaging apparatus 40 may be a camera, for example. In some embodiments, there may be more than one imaging apparatus 40, for example, operating together for generating a composite image based upon collected images from each of the imaging apparatuses. The imaging apparatus 40 may be in the form of a handheld scanner, for example. The medication inventory system 20 includes a controller 49. The controller 49 includes a processor 41 and an associated memory 42. The controller 49 may be carried by the support table 21, for example, or in a housing with the imaging apparatus 40. The controller 49 may be remote from the support table 21 and imaging apparatus 40, for example, in a cloud computing environment.

A display 43 is coupled to the controller 49. The display 43 may be carried by or adjacent the support table 21 and/or the arm 22. The display 43 may be remote from the support table 21, for example, a remote display and/or a display of a mobile wireless communications device, such as, for example, a mobile telephone or tablet computer. The controller 49 may be carried within the housing of the display 43. The controller 49 may be located remote from the imaging apparatus 40 and/or display 43, for example, as part of a cloud server in a cloud computing environment.

Figure 3:
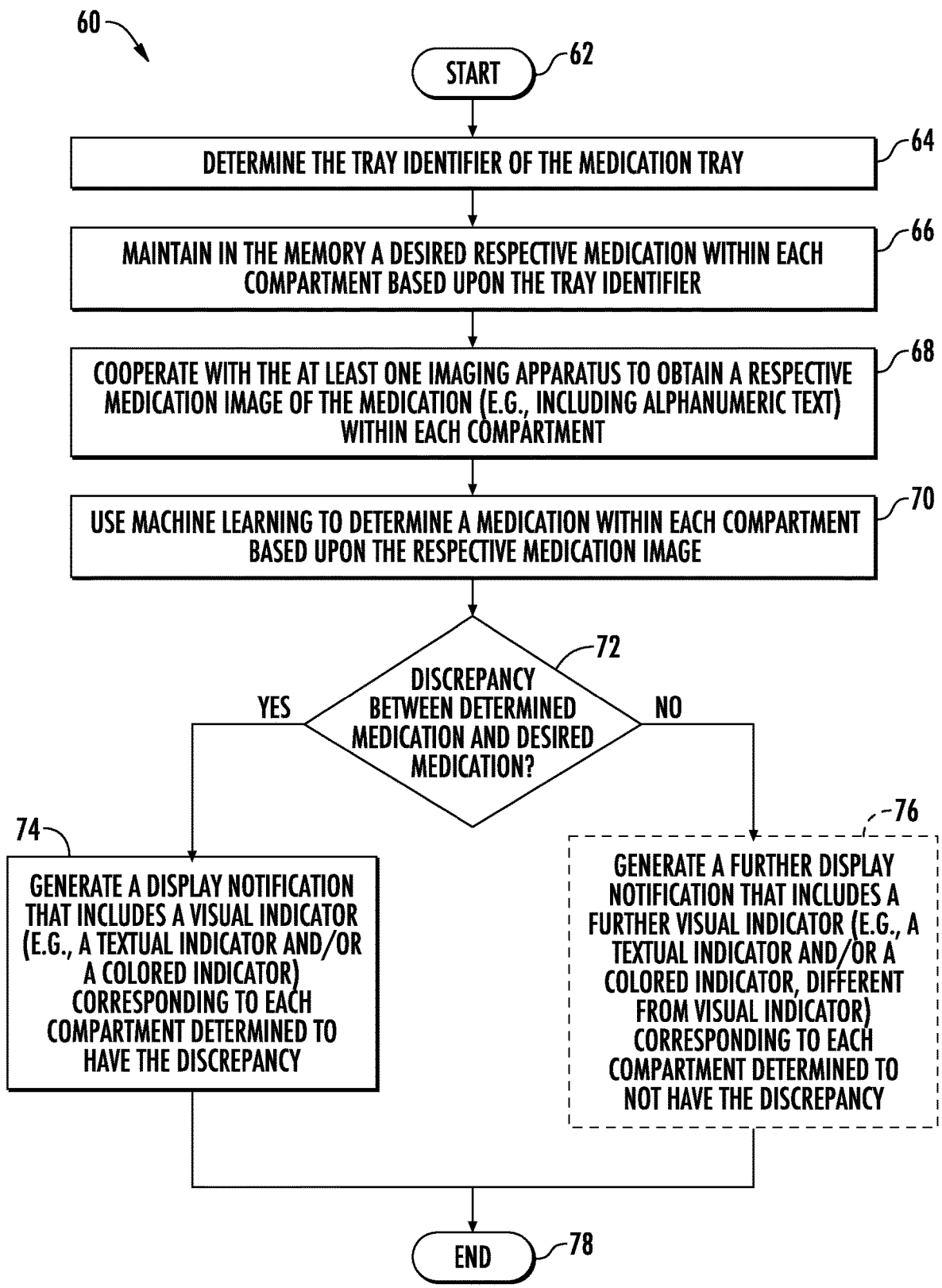
FIG. 3 is a flow diagram of operation of the medication inventory system of FIG. 1.

Referring now to the flowchart 60 in FIG. 3, beginning at Block 62, operations of the medication inventory system 20 will now be described with respect to operations of the controller 49. At Block 64, the controller 49 cooperates with the imaging apparatus 40 to determine the tray identifier of the medication tray. More particularly, the tray identifier 31 is optically sensed or scanned by the imaging apparatus 40. The controller 49 cooperates to identify the particular medication tray 30 based upon the tray identifier 31.

The controller 49 maintains, in the memory 42, a desired respective medication within each compartment 32a-32h based upon the tray identifier (Block 66). More particularly, the memory 42 includes a reference, mapping, or configurations of which medications are desired or expected within each of the compartments 32a-32h for the given tray associated with the tray identifier 31. As will be appreciated by those skilled in the art, a different configuration or expected medication may be within each compartment for different tray identifiers.

At Block 68, the controller 49 cooperates with the imaging apparatus 40 to obtain a respective medication image of the medication 33 within each compartment 32a-32h. More than one medication image may be obtained of a given medication in a corresponding compartment 32a-32h.

The controller 49 uses machine learning to determine a medication 33 within each compartment 32a-32h based upon the respective medication image (Block 70). More particularly, the controller 49 may learn physical characteristics or traits of different medications, for example, as they appear within an obtained medication image, to determine the medication 33. For example, each respective medication image may include alphanumeric text so that the processor 41 may perform an optical character recognition (OCR) of the alphanumeric text to determine the respective medication within each compartment 32a-32h. The alphanumeric text may include a lot number, medication identifier, expiration date, etc. Each respective medication 33 also has a size, shape, and color. The processor 41 may use the size, shape, and color of each medication 33 to determine the medication within each compartment 32a-32h. The processor 41 may also use the orientation, pose, and/or image parameters to determine the medication 33 within each compartment 32a-32h. These physical characteristics may be fed as input to train a learning function. Other input, for example, the alphanumeric text, may be used to train the learning function. Those skilled in the art will appreciate that other factors may be used to train the learning function and thus serve as a basis to determine the medication, such as, for example, physical similarity to other medications, relative position within the medication tray 30, and/or often-confused-for medications. The processor 41 may use other and/or additional recognition techniques, as will be appreciated by those skilled in the art. For example, the processor 41 may use more than one learning function in addition to OCR.

At Block 72, a determination is made as to whether there is a discrepancy between the determined medication 33 within each compartment 32a-32h and the desired respective medication within each compartment. In particular, the determined medication within each compartment 32a-32h is compared or matched to the desired respective medication stored in the memory 42. Those skilled in the art will appreciate that the identifying data from the medication determination may be matched to corresponding stored desired medication data, and/or the obtained images may be matched to reference images of medications 33 stored in the memory 42. A discrepancy may be determined when a threshold amount of matched data is not exceeded. In other words, if the processor 41 cannot determine within a threshold amount of certainty, for example, less than 100%, that the determined medication 33 (as determined based upon machine learning) matches the expected medication for a given compartment, the processor may determine that there is a discrepancy. In other words, a mismatch of medication 33 may be determined.

If at Block 72 it is determined that there is discrepancy between the determined medication within each compartment 32a-32h and the desired respective medication with each compartment, the controller 49 generates a display notification 44 that includes a visual indicator 45 corresponding to each compartment determined to have a discrepancy (Block 74). The display notification 44 may include an image of the medication tray 30 with the corresponding visual indicators 45 overlaid thereon. The display notification 44 may, in some embodiments, also include further visual indicators 46 having one or more different visual characteristics that correspond to each compartment 32a-32h that does not have a discrepancy (Block 76). The visual indicators 45 may be in the form of a textual indictor (e.g., "OK", or "DISCREPANCY") and/or a colored indictor (e.g., a red box overlaid corresponding compartments having a discrepancy and a green box overlaid corresponding compartments not having a discrepancy). Upon a discrepancy, the controller 49 may display or provide an indication of the expected medication, and in some instances recommend a substitute medication (e.g., a generic or similarly performing). Operations end at Block 78. Of course, in some embodiments, if there are no discrepancies, no display notification may be displayed and the operations may end at Block 78.

Figure 4:
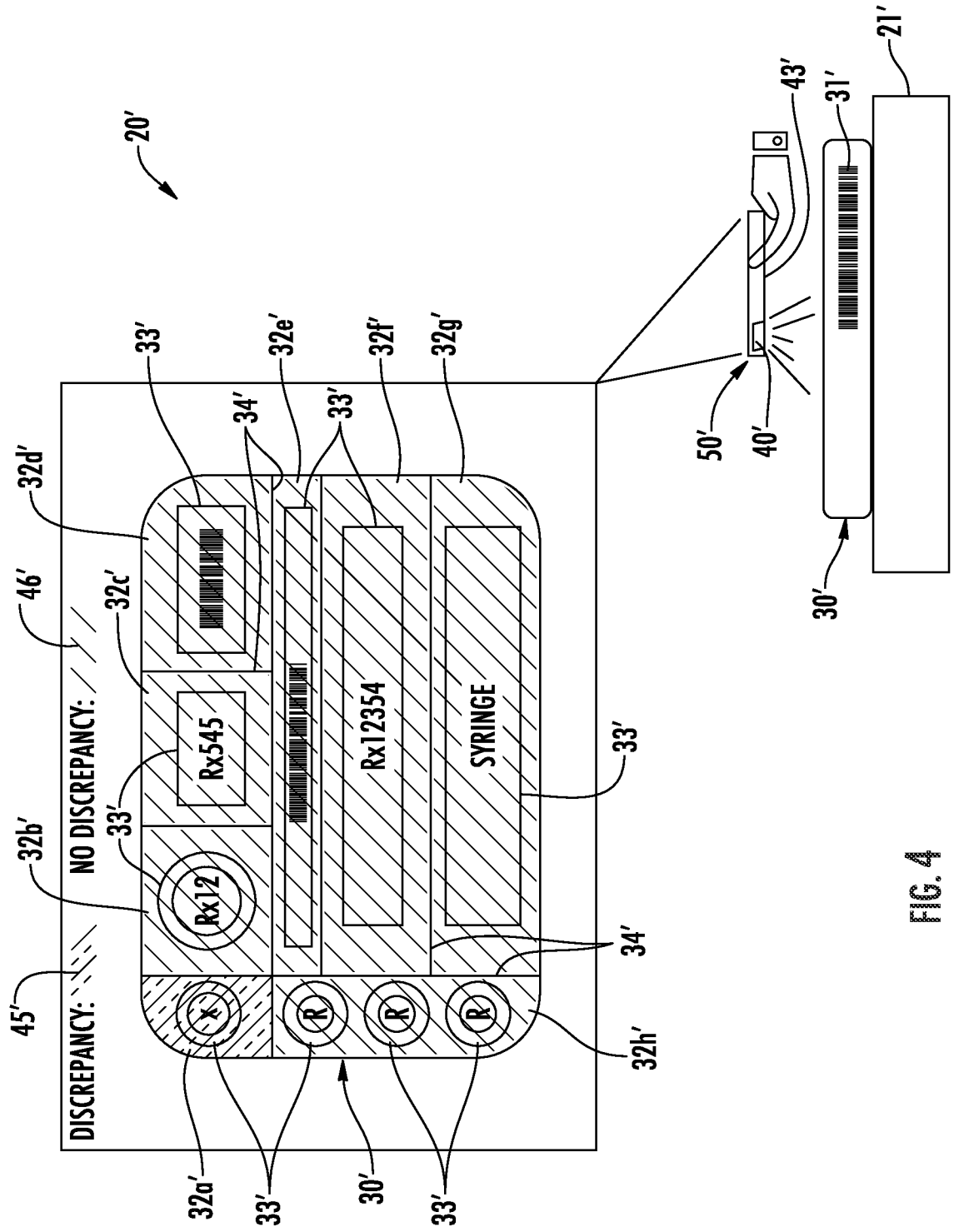
FIG. 4 is a schematic diagram of a medication inventory system according to another embodiment.
Figure 5:
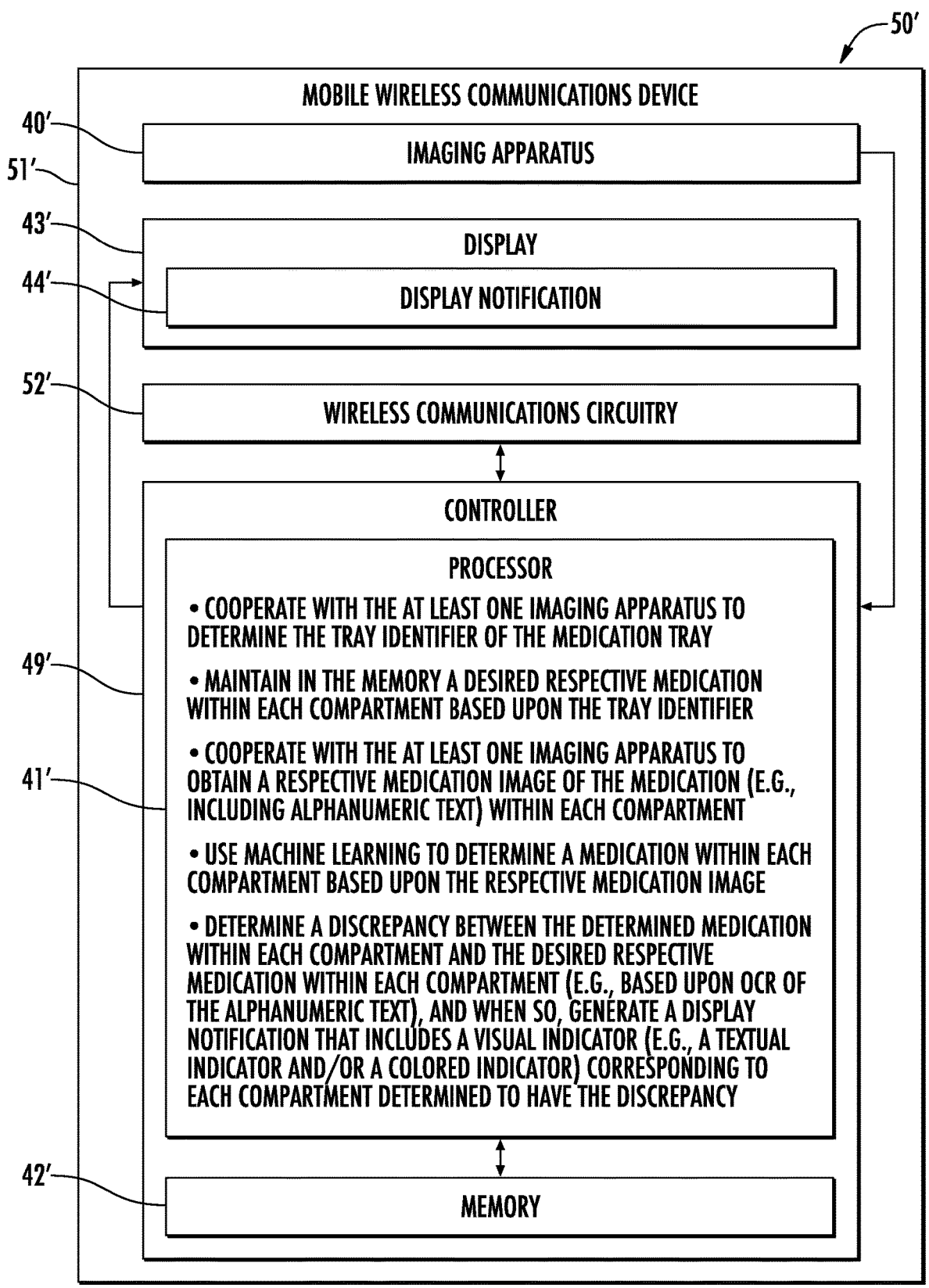
FIG. 5 is a schematic block diagram of the medication inventory system of FIG. 4.

Referring now to FIGS. 4-5, in another embodiment, the medication inventory system 20' includes a mobile wireless communications device 50' that includes a housing 51' and wireless communications circuitry 52' carried by the housing. The mobile wireless communications device 50' may be in the form of a mobile telephone or tablet computer, for example. Of course, the mobile wireless communications device may be in the form of another type of device. The wireless communications circuitry 52' may include long and short-range wireless communications circuitry, for example, cellular, WiFi, near-field communications (NFC), and/or Bluetooth®. The imaging apparatus 40' is also carried by the housing 51' opposite a display 53' also carried by the housing. The controller 49' is also carried by the housing 51'. In the present embodiment, a user associated with the mobile wireless communications device 50' may manually move the mobile wireless communications device over the top of the medication tray 30' with the imaging apparatus 40' pointed toward the medication tray to obtain the respective medication images and the tray identifier 31' (e.g., within the field of view as the mobile wireless communications is moved). The mobile wireless communications device 50' may be carried by or coupled to the arm if the manual movement by the user is not desired. During operation, as the user manually moves the mobile wireless communications device 50' over or across the top of the medication tray 30' acquiring images (imaging device facing the medication tray) any display notifications 44' including corresponding visual indicators 45' may be displayed on the display 53' (facing the user and carried by the housing 51' opposite the imaging device 40').

Figure 6:
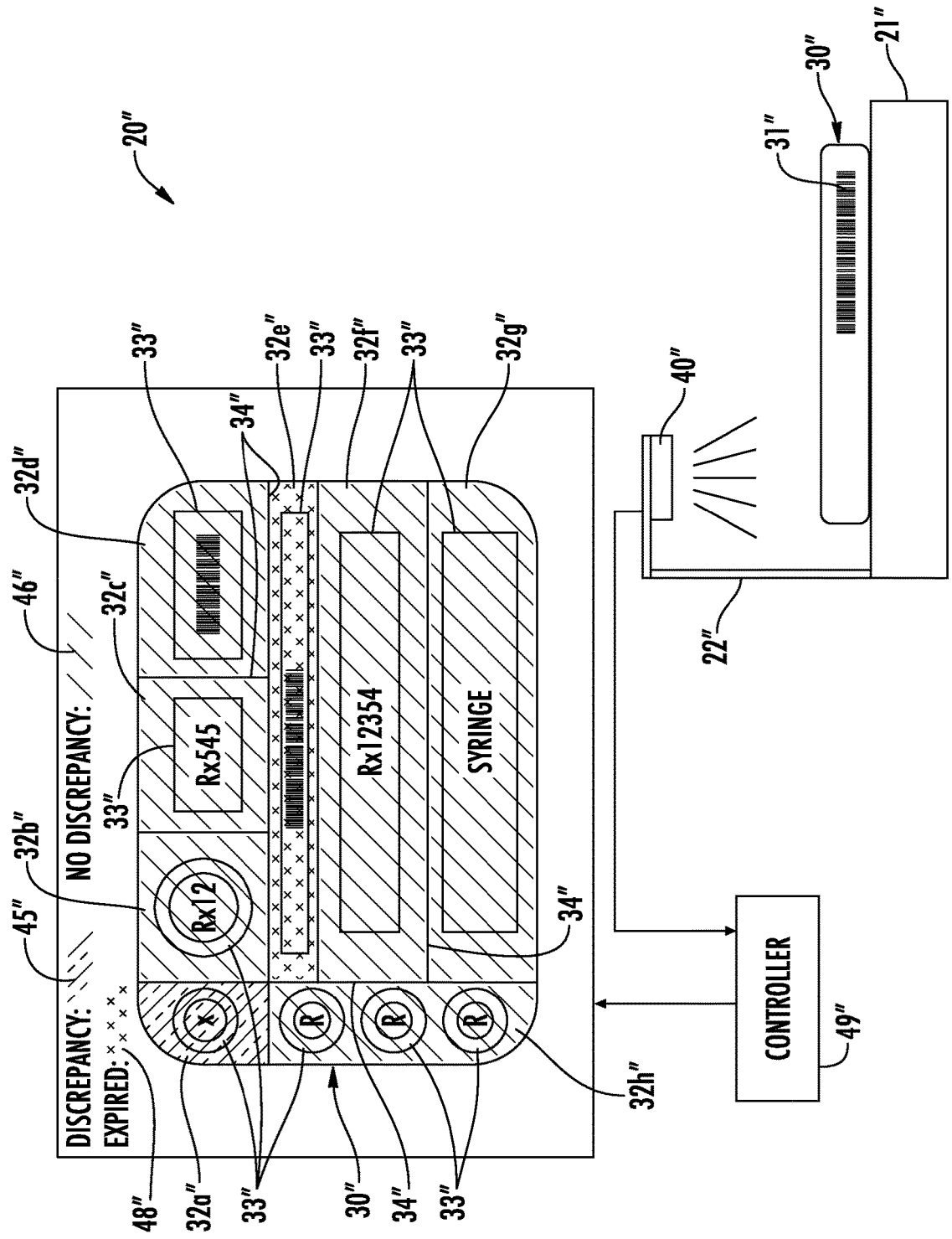
FIG. 6 is a schematic diagram of a medication inventory system according to another embodiment.
Figure 7:
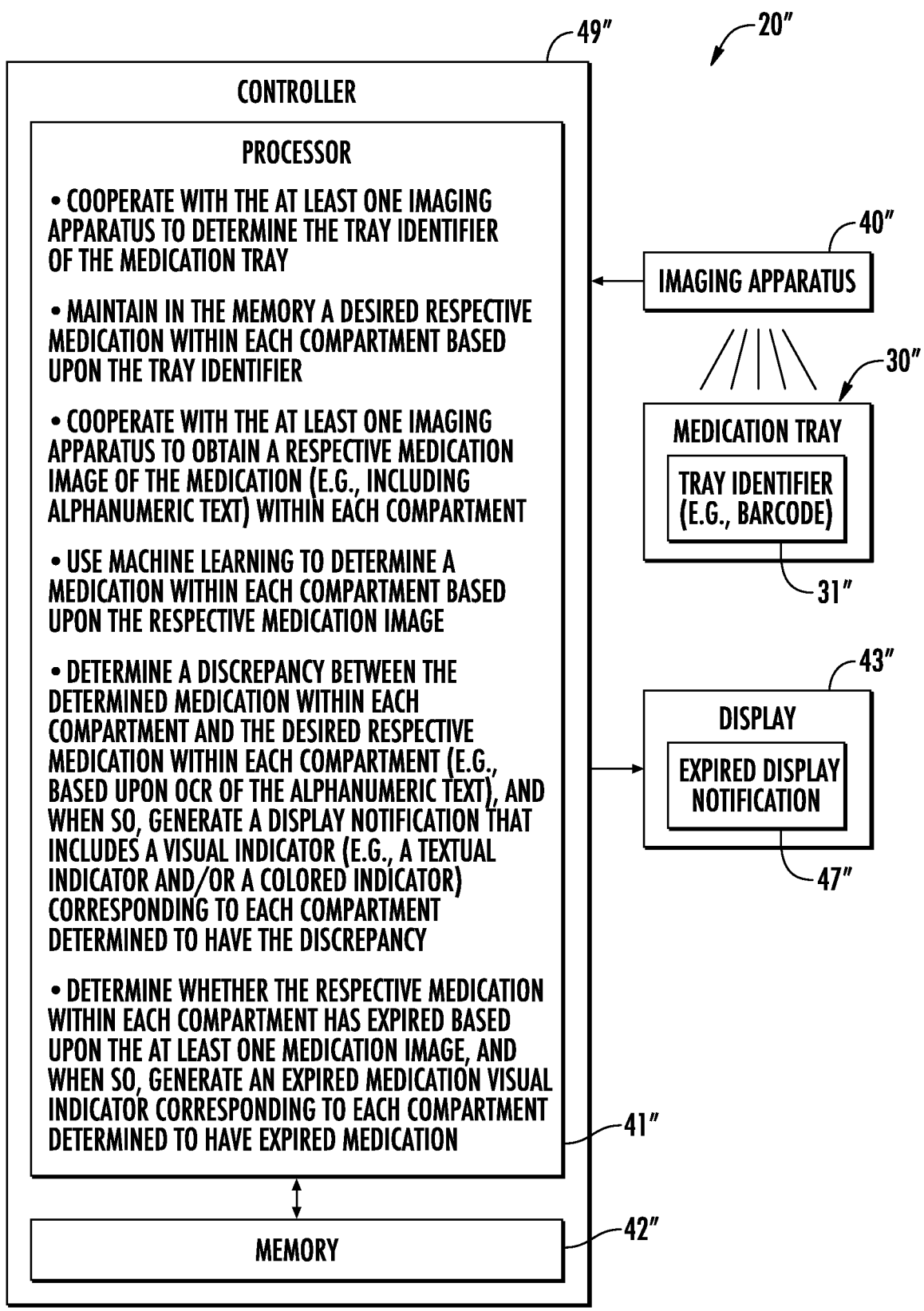
FIG. 7 is a schematic block diagram of the medication inventory system of FIG. 6.

Referring now to FIGS. 6 and 7, in another embodiment, the controller 49" determines whether the respective medication 33" within each compartment 32a"-32h" has expired based upon the medication image. When a respective medication is determined to have expired, the controller 49" generates an expired medication display notification 47" that includes an expired medication visual indicator 48" corresponding to the each compartment determined to have expired medication. The expired medication display notification 47" may be similar (e.g., colored indicator and/or textual) to the notification described above with respect a determined discrepancy, but may have different visual characteristics. In some embodiments, the expired medication visual indicator 48" may be integrated within the display notification 44" of a discrepancy. For example, the visual indicator 45" included within the display notification 44" may indicate the type of discrepancy by way of the visual characteristics (e.g., expired, not expected medication).

Figure 8:
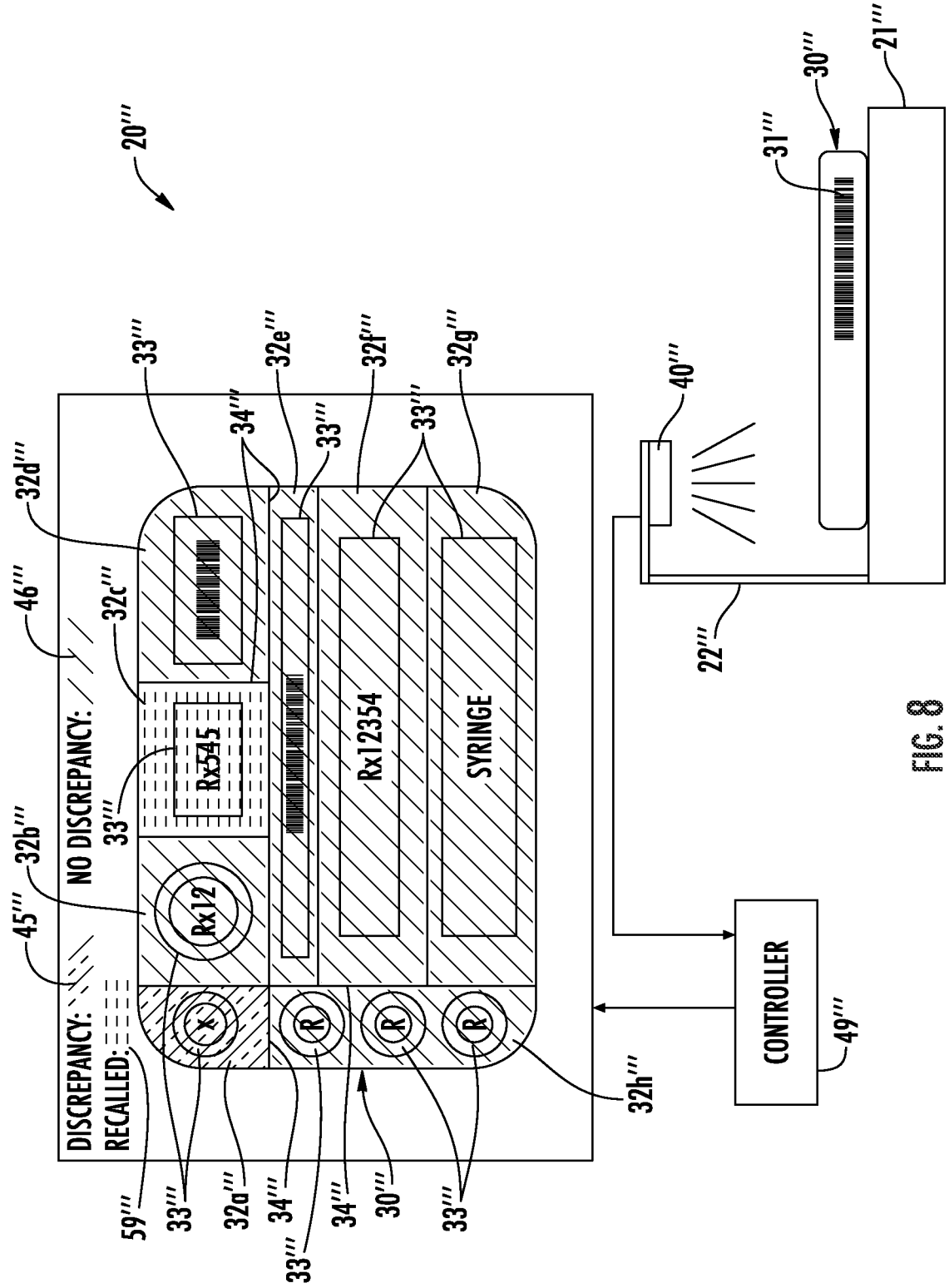
FIG. 8 is a schematic diagram of a medication inventory system according to another embodiment.
Figure 9:
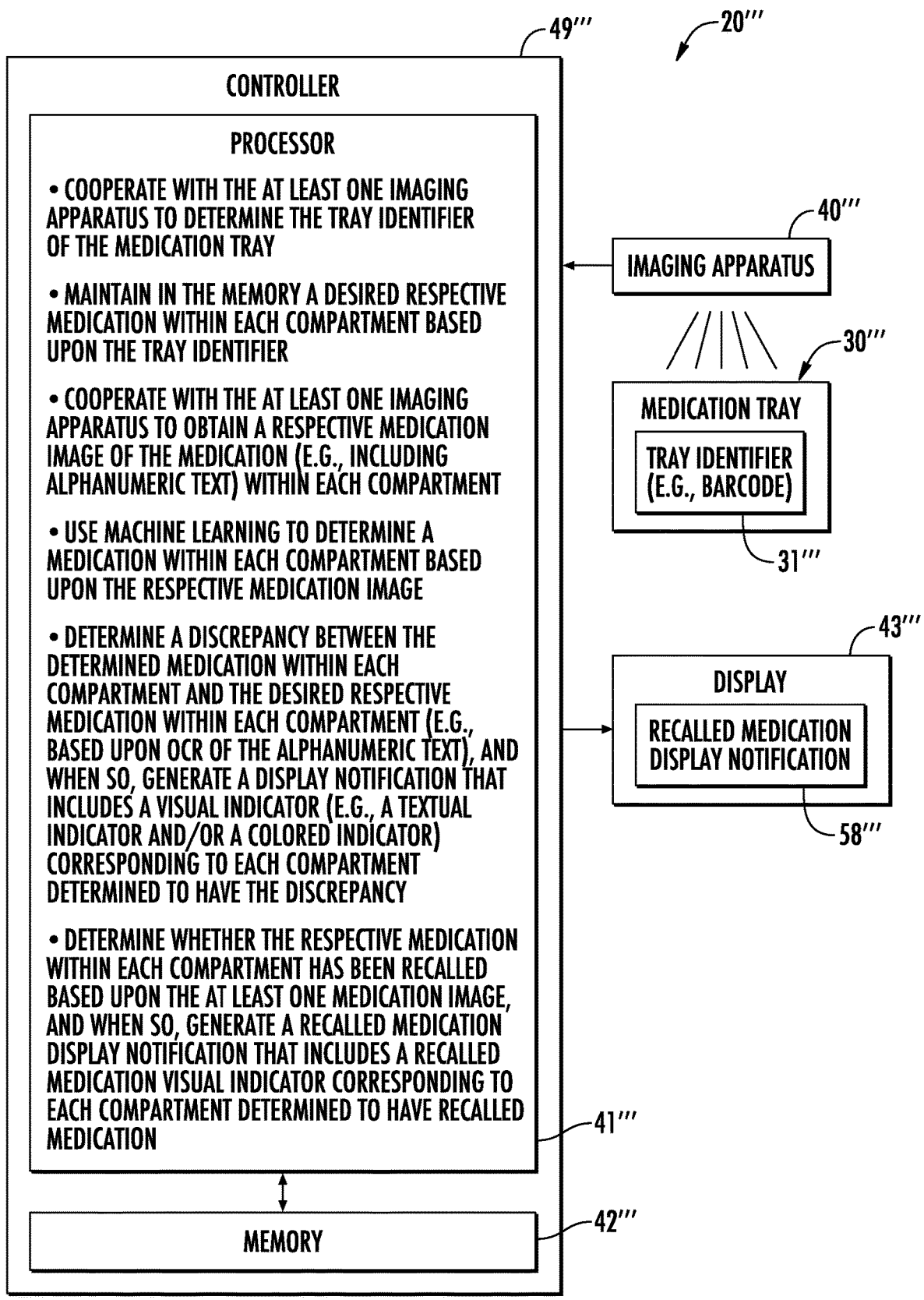
FIG. 9 is a schematic block diagram of the medication inventory system of FIG. 8.
Figure 10:
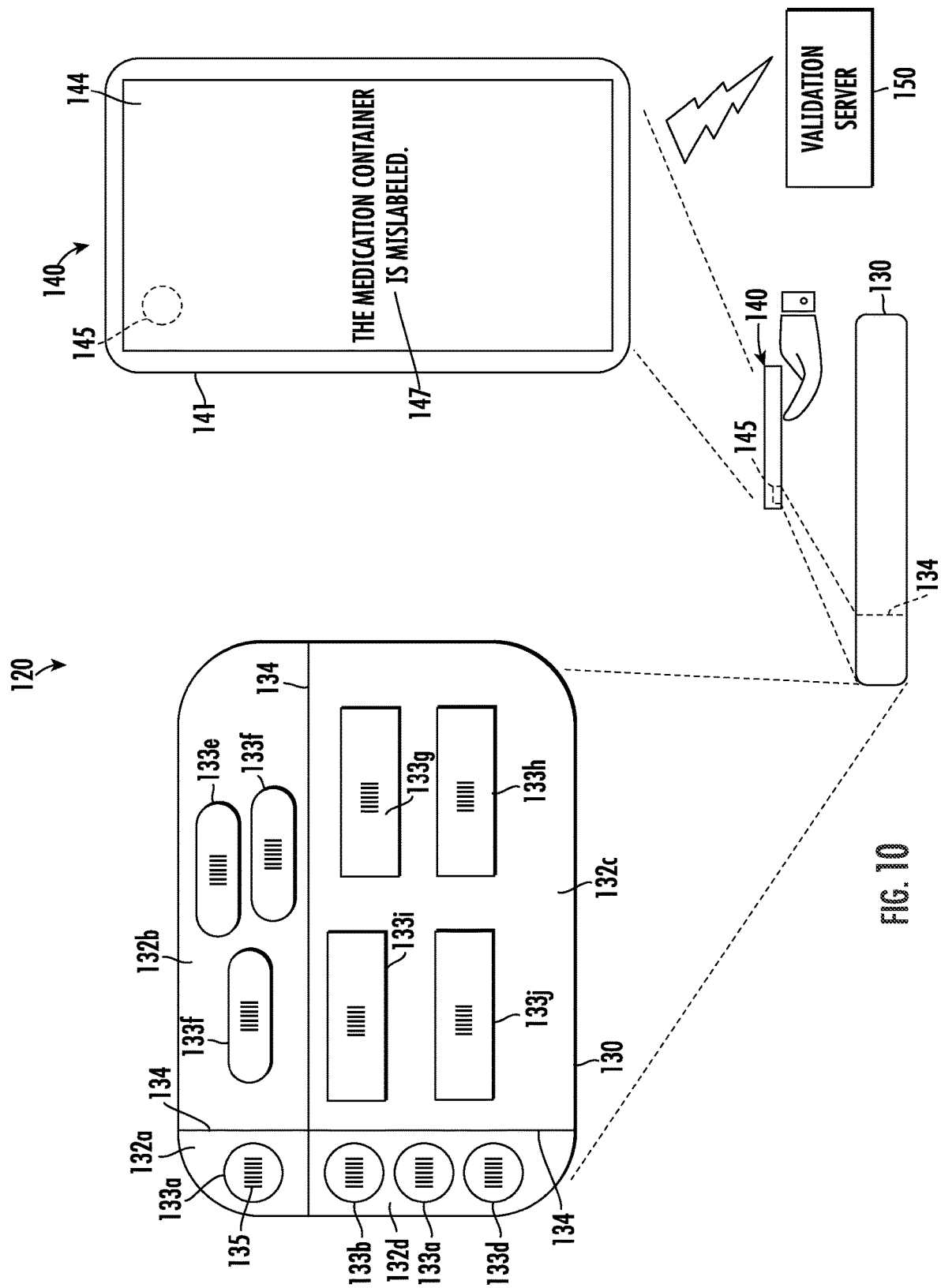
FIG. 10 is a schematic diagram of a medication validation system according to an embodiment.
Figure 11:
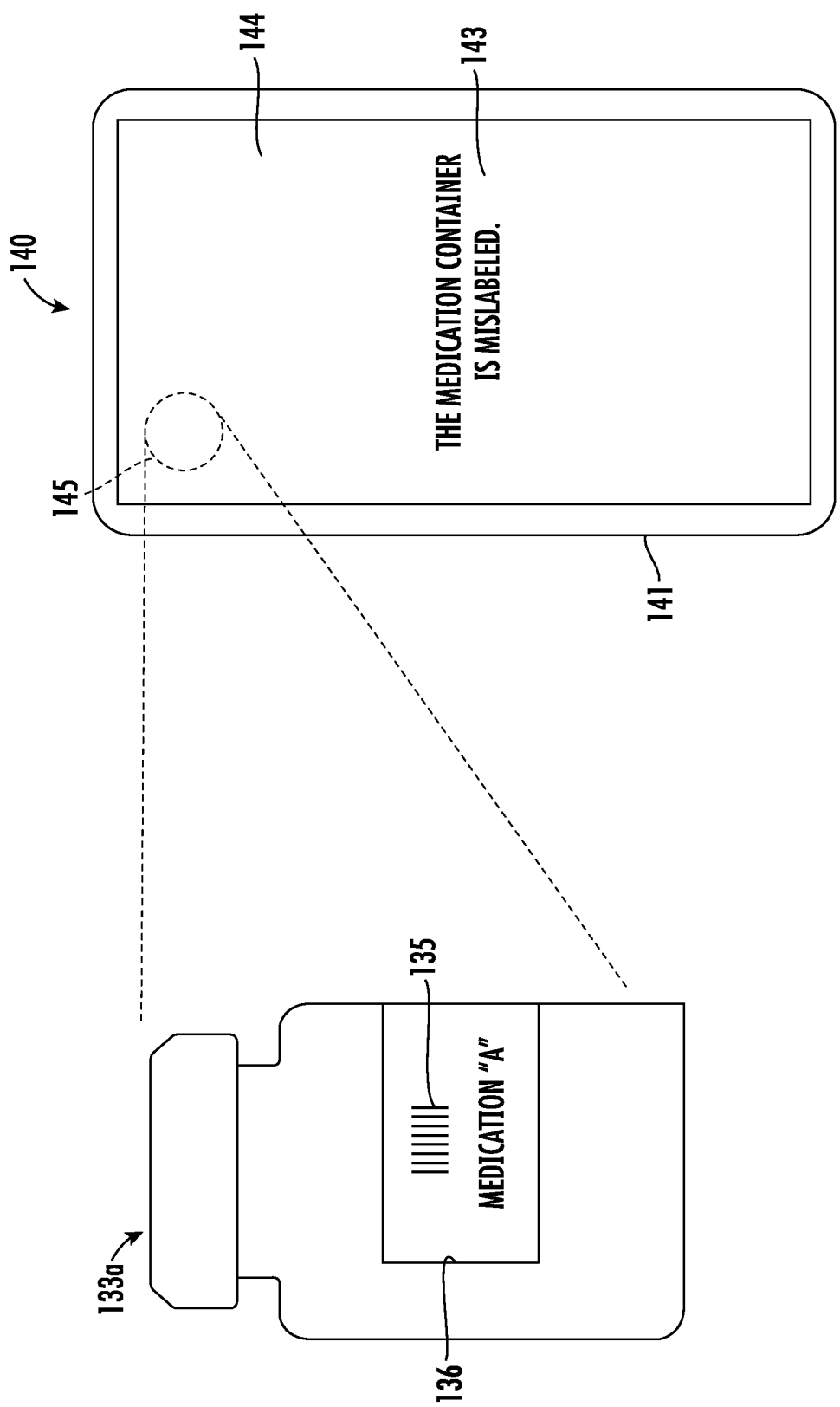
FIG. 11 is a schematic diagram of a portion of the medication validation system of FIG. 10.
Figure 12:
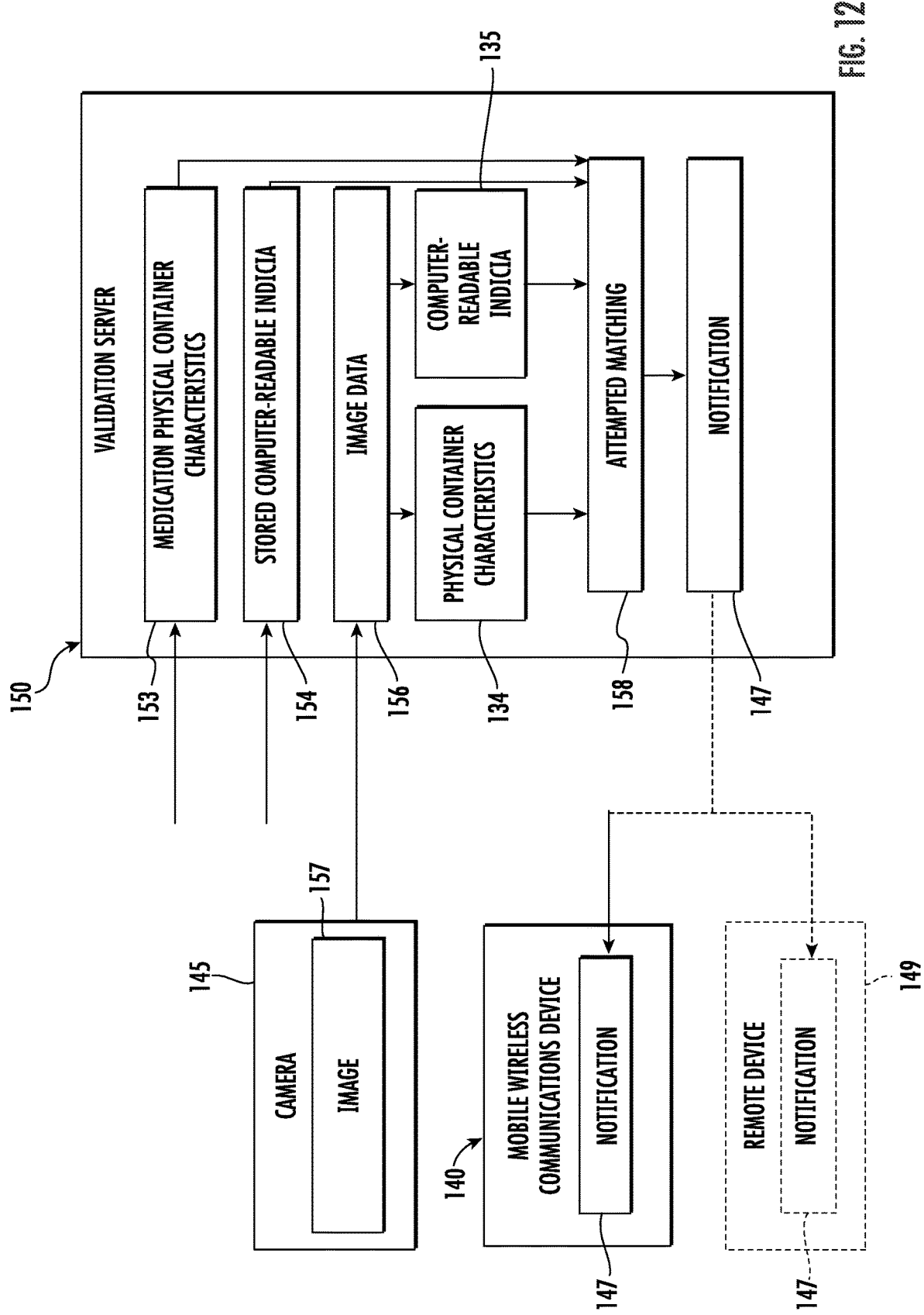
FIG. 12 is another schematic diagram of the medication validation system of FIG. 10.
Figure 13:
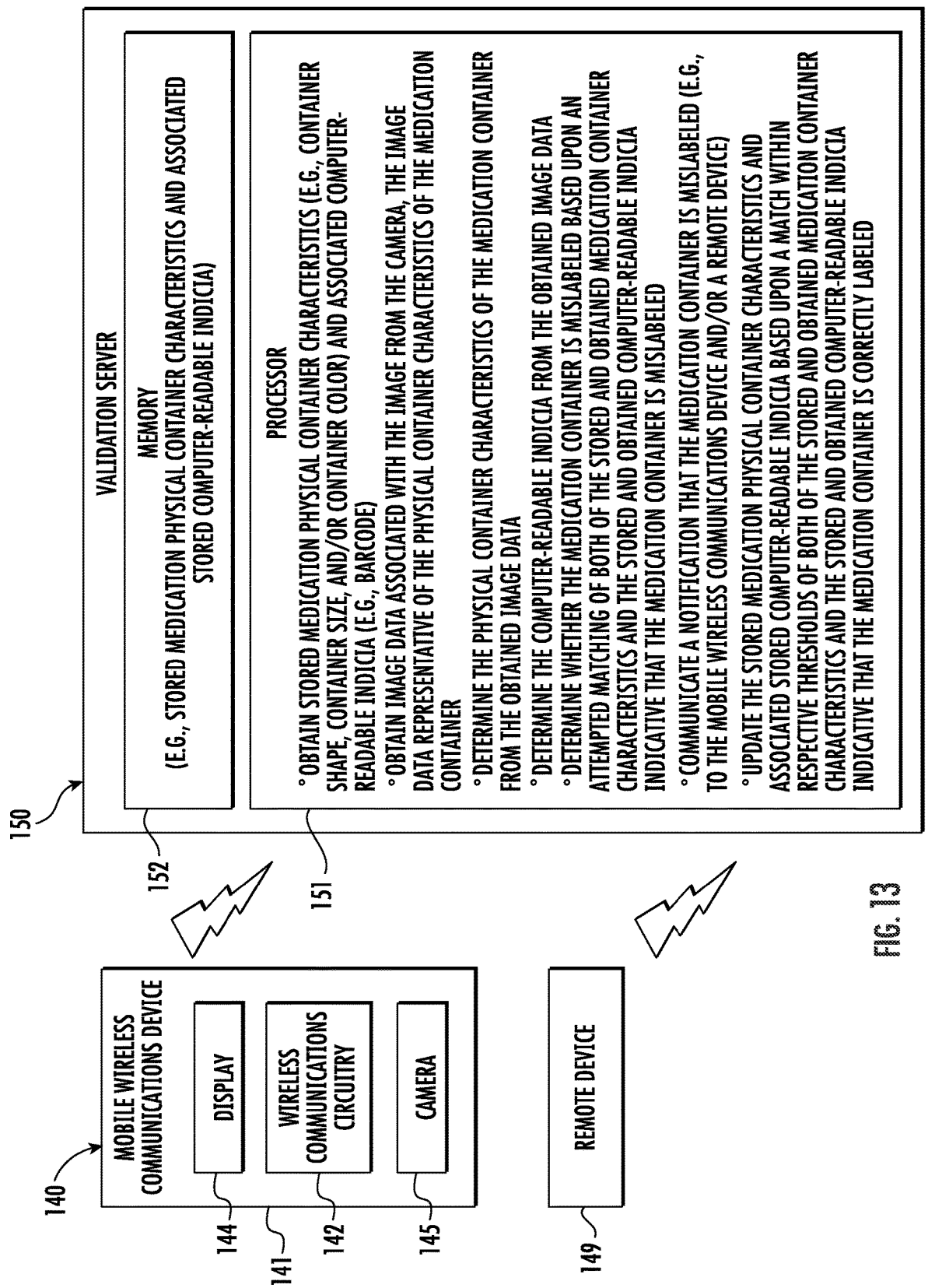
FIG. 13 is a schematic block diagram of a medication validation system of FIG. 10.

Referring now to FIGS. 8 and 9, in another embodiment, the controller 49''' determines whether the respective medication within each compartment 32a'''-32h''' has been recalled based upon the medication image. When a respective medication 33''' is determined to have been recalled, the controller 49''' generates a recalled medication display notification 58''' that includes a recalled medication visual indicator 59''' corresponding to each compartment 32a'''-32h''' determined to have recalled medication. The recalled medication display notification 58''' may be similar (e.g., colored indicator and/or textual) to the notification 44 described above with respect a determined discrepancy, but may have different visual characteristics. In some embodiments, the recalled medication visual indicator 59''' may be integrated within the display notification 44 and/or expired medication notification 47". For example, the visual indicator included within the display notification 44 may indicate the type of discrepancy by way of the visual characteristics (e.g., recalled, not expected medication, expired).

The medication inventory system 20 may be advantageous for providing increased accuracy loading or packing of medication 33 within the compartments 32a-32h of a given medication tray 30. More particularly, the medication inventory system 20 described herein may be particularly advantageous for confirming medications 33 within a crash cart, which typically includes medications for emergency treatment. As will be appreciated by those skilled in the art, items within a crash cart are typically located in the same compartment within a tray among different crash carts within a given hospital or hospital system. Medical professionals may typically, in an emergency situation, reach for a medication 33 within a given compartment without inspection of the medication to confirm the accuracy of the medication within the compartment. Accordingly, a misplaced medication 33 or a discrepancy of what is expected within a compartment and what is actually within the compartment may have far reaching implications. The system 20 described herein may address these shortcomings by providing confirmation that the expected medications match the actual medications within a compartment, and by providing notification when there is a discrepancy.

A method aspect is directed to a method of managing medication in a medication inventory system 20 that includes a medication tray 30 including a plurality of partitions 34 defining a plurality of compartments 32a-32h. The medication tray 30 has a tray identifier 31 associated therewith, and each compartment 32a-32h is for storing a respective medication 33. The method includes using a processor 41 and an associated memory 42 configured to cooperate with at least one imaging apparatus 40 to determine the tray identifier 31 of the medication tray 30 and maintain in the memory a desired respective medication within each compartment based upon the tray identifier. The method also includes using the processor 41 and associated memory 42 to cooperate with the at least one imaging apparatus 40 to obtain a respective medication image of the medication 33 within each compartment 32a-32h and use machine learning to determine a medication within each compartment based upon the respective medication image. The method also includes using the processor 41 and associated memory 42 to determine a discrepancy between the determined medication 33 within each compartment and the desired respective medication within each compartment, and when so generate a display notification 44 that includes a visual indicator 45 corresponding to each compartment determined to have the discrepancy.

A computer readable medium aspect is directed to a non-transitory computer readable medium for managing medication in a medication inventory system 20 that includes a medication tray 30 including a plurality of partitions 34 defining a plurality of compartments 32a-32h. The medication tray 30 may have a tray identifier 31 associated therewith, and each compartment 32a-32h is for storing a respective medication 33. The non-transitory computer readable medium may include computer executable instructions that when executed by a processor 41 cause the processor to perform operations. The operations include cooperating with at least one imaging apparatus 40 to determine the tray identifier 31 of the medication tray 30 and maintaining in a memory 42 a desired respective medication within each compartment 32a-32h based upon the tray identifier 31. The operations also include cooperating with the at least one imaging apparatus 40 to obtain a respective medication image of the medication 33 within each compartment 32a-32h, and using machine learning to determine a medication within each compartment based upon the respective medication image. The operations further include determining a discrepancy between the determined medication 33 within each compartment and the desired respective medication within each compartment, and when so generating a display notification 44 that includes a visual indicator 45 corresponding to each compartment determined to have the discrepancy.

Referring now to FIGS. 10-13, in another embodiment, a medication validation system 120 includes a camera 145 that captures an image of a medication container 133. The camera 145 is illustratively carried by a housing 141 of a mobile wireless communications device 140. The mobile wireless communications device 140 also includes wireless communications circuitry 142 and a display 144 carried by the housing 141. The mobile wireless communications device 140 is illustratively in the form of mobile phone. The mobile wireless communications device 140 may be in the form of another mobile wireless communications device, for example, a tablet computer or a wearable device. Of course, the mobile wireless communications device 140 may be a camera device with wireless communications capabilities, as will be appreciated by those skilled in the art.

The medication container 133 may be a pill container, a vile, a box or packaging of a medication, or other container as will be appreciated by those skilled in the art.

The medication container 133 may be carried by a medication tray 130, for example. The medication tray 130 illustratively includes partitions 134 defining compartments 132a-132d. Other medication containers 133b-133j are carried within the compartments 132b-132d. The medication container 133a is carried within one of the compartments. In other words, one of the compartments 132a-132d is for storing the medication container 133a.

The medication container 133a has physical container characteristics associated therewith. Physical container characteristics may include any one or more of container shape, container size, container color, rim features, neck features, imprinting or embossing features, etc.

The medication container 133a illustratively has a computer-readable indicia 135 affixed thereon. The computer-readable indicia 135 may include a barcode, for example. The computer-readable indicia 135 may be another type of indicia, for example, a quick-response (QR) code or other type of computer-readable indicia. The computer-readable indicia 135 may be printed on a label 136 that is affixed to the medication container 133. The label 136 may have text 137 printed thereon, for example, in addition to the computer-readable indicia 135.

The medication validation system 120 also includes a validation server 150. The validation server 150 includes a processor 151 and an associated memory 152. While operations of the validation server 150 are described herein, it should be understood that the operations of the validation server 150 are performed through cooperation between the processor 151 and the memory 152.

Figure 14:
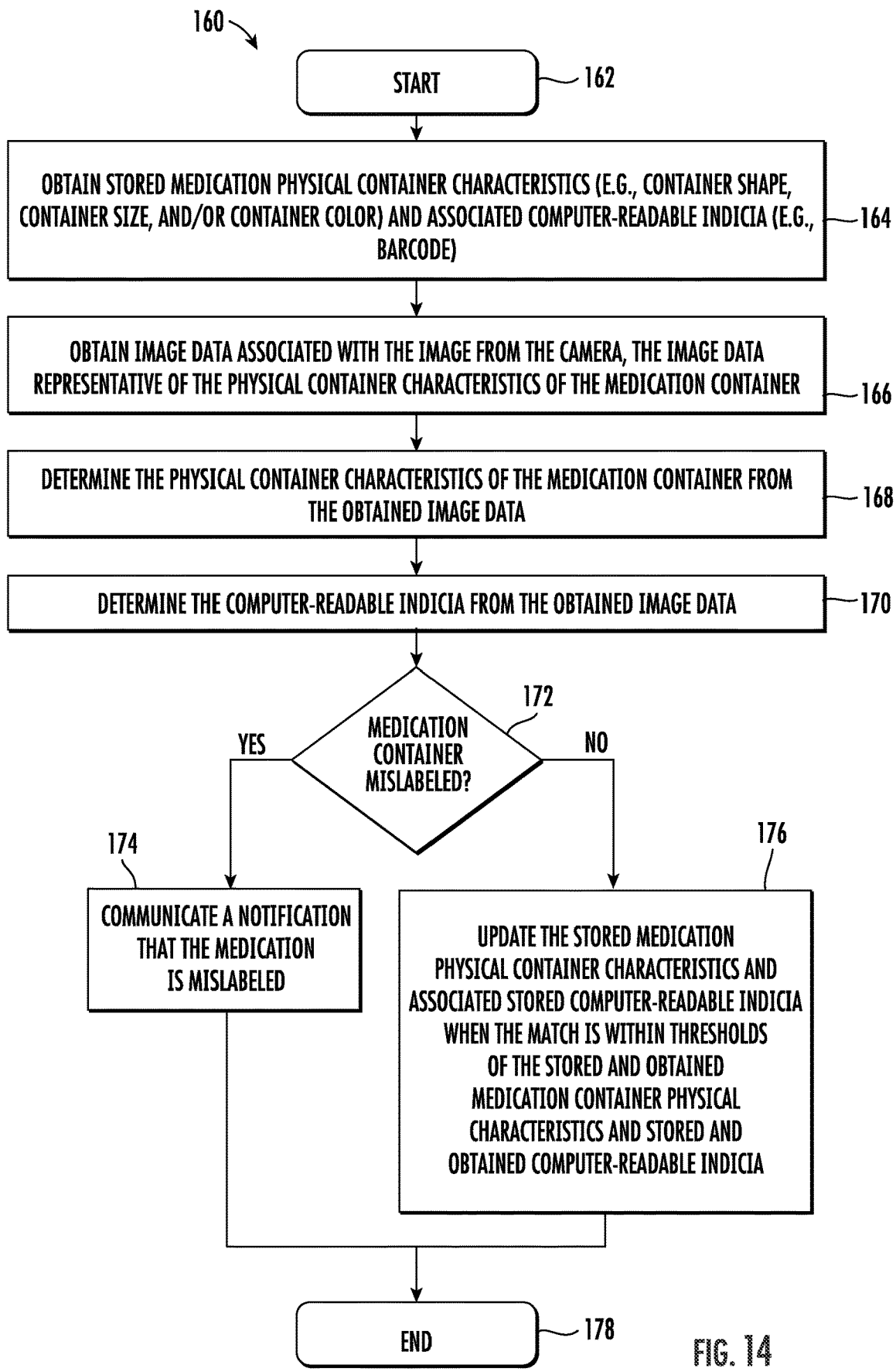
FIG. 14 is a flow diagram illustrative operation of the validation server of the medication validation system of FIG. 10.

Referring now additionally to the flowchart 160 in FIG. 14, beginning at Block 162, operations of the validation server 150 with respect to validating a medication will now be described. At Block 164 the validation server 150 obtains stored medication physical container characteristics 153 and associated stored computer-readable indicia 154. The stored medication physical container characteristics 153 and associated stored computer-readable indicia 154 may be obtained from the memory 152 and/or from remote servers, such as, for example, manufacturers databases associated with the medication container 133a. The validation server 150 may learn the stored medication physical container characteristics 153 and associated stored computer-readable indicia 154 by updating the stored the medication physical container characteristics and associated stored computer-readable indicia from a baseline based upon various sources, such as, for example, the camera 140 and/or the Internet.

The validation server 150 obtains image data 142 associated with the image from the camera 145, for example, wirelessly via the wireless communications circuitry 142 (Block 166). The validation server 150 may retrieve, or the camera 145 may communicate or send, the image data to the validation server, for example, upon acquisition or capture of the image 157. The validation server, at Block 168, determines the physical container characteristics 134 of the medication container 133 from the image data 156. The physical container characteristics 134 may be determined via a classifier, for example, as will be appreciated by those skilled in the art. In other words, the validation server 150 may determine a shape, size, and/or color of the medication container 133a from the image data 156 based upon, for example, identifying boundaries of medication container.

At Block 170, the validation server 150 determines the computer-readable indicia 135 from the obtained image data 156. The computer-readable indicia 135 may be obtained similarly to the physical container characteristics 134. For example, the validation server 150 may identify a barcode or a QR code in the image data 156. The validation server 150 may obtain or retrieve medication container data associated with the determined computer-readable indicia 135, for example, associated physical container characteristics 134.

The validation server 150 determines whether the medication container 133a is mislabeled based upon an attempted matching 158 of both of the stored and obtained medication container characteristics 153, 134 and the stored and obtained computer-readable indicia 154, 135 indicative that the medication container 133a is mislabeled (Block 172). More particularly, if there is a match between both of the stored and obtained medication container characteristics 153, 134 and the stored and obtained computer-readable indicia 154, 135, the validation server 150 determines that the medication container 133 is not mislabeled. Alternatively, if, based upon an attempted matching, there is no match between both of the stored and obtained medication container characteristics 153, 134 and the stored and obtained computer-readable indicia 154, 135, then the validation server 150 determines that the medication container 133 is mislabeled.

To determine the match, the validation server 150 may, for example, with respect to container shape, align and overlay data representative of the image to determine a match to within a threshold degree of certainty. In some embodiments, if the medication container shape is identified by the validation server 150 as being likely associated with any number of medications (e.g., medication A, B, C, etc.), the validation server may determine a match when both of the stored and obtained medication container characteristics 153, 134 identify the medication as being the same (e.g., A, B, C, etc.).

The validation server 150 may identify a match or mismatch based upon a threshold number of matching physical characteristics. In other words, if 9 of 10 physical characteristics are determined to be matching, the validation server 150 may determine a characteristic match. Similarly, if the validation server 150 determines that the stored and obtained computer-readable indicia 154, 135 match, for example, to within a threshold degree of certainty. In an embodiment, if there is both a characteristic match and a computer-readable indicia 154, 135 match, the validation server 150 may determine that the medication container is labeled correctly. Of course, other and/or additional techniques may be used to determine whether the medication container 133a is mislabeled. For example, text from the label 136 affixed to the medication container 133a may be optically recognized based upon the image data 156 and used as a basis also for an attempted matching.

If, at Block 172, the validation server 150 determines that the medication container 133a is mislabeled, the validation server communicates a notification 144 that the medication container is mislabeled (Block 174). The validation server 150 may communicate the notification 147 to the mobile wireless communications device 140, for example, for display thereon. In an embodiment, the validation server 150 may alternatively or additionally communicate the notification 147 to remote device 149, for example, a remote computer, a remote server, or a remote mobile wireless communications device.

If, at Block 172, the validation server 150 determines the medication container 133a is not mislabeled (labeled correctly), for example, both of the stored and obtained medication container characteristics 153, 134 and the stored and obtained computer-readable indicia 154, 135 match to within a threshold certainty that the medication container is correctly labeled, the validation server may update the stored medication container characteristics 153 and the stored computer-readable indicia 154 (Block 176). More particularly, the validation server 150 applies machine learning so that as obtained medication container characteristics 134 and computer-readable indicia 135 are obtained and determined to be part of a correctly labeled medication container 133a, small changes or variations may be considered for the attempted matching. The machine learning may also be applied to achieve an increased level of certainty at which the validation server determines that the medication container 133a is not mislabeled (i.e., correctly labeled). Operations end at Block 178.

A method aspect is directed to a method of validating a medication. The method includes using a validation server 150 to obtain stored medication physical container characteristics 153 and associated stored computer-readable indicia 154, and obtain image data 156 associated with an image 141 of a medication container 133*a* from a camera 145. The image data 156 may be representative of physical container characteristics 134 of the medication container 133, and the medication container may have a computer readable indicia 135 affixed thereon. The method includes using the validation server 150 to determine the physical container characteristics 134 of the medication container 133*a* from the obtained image data 156, and determine the computer-readable indicia 135 from the obtained image data. The method further includes using the validation server 150 to determine whether the medication container 133 is mislabeled based upon an attempted matching of both of the stored and obtained medication container characteristics 153, 134 and the stored and obtained computer-readable indicia 154, 135 indicative that the medication container is mislabeled, and communicate a notification 144 that the medication container is mislabeled.

A computer readable medium aspect is directed to a non-transitory computer readable medium for validating a medication. The non-transitory computer readable medium includes computer executable instructions that when executed by a processor 151 of a validation server 150 cause the processor to perform operations. The operations include obtaining a plurality of stored medication physical container characteristics 153 and associated stored computer-readable indicia 154, and obtaining image data 156 associated with an image 157 of a medication container 133*a* from a camera 145. The image data 156 is representative of physical container characteristics 134 of the medication container 133*a*. The medication container 133*a* has a computer-readable indicia 135 affixed thereon. The operations include determining the physical container characteristics 134 of the medication container 133*a* from the obtained image data 156, and determining the computer-readable indicia 135 from the obtained image data 141. The operations also include determining whether the medication container 133*a* is mislabeled based upon an attempted matching of both of the stored and obtained medication container characteristics 153, 134 and the stored and obtained computer-readable indicia 154, 135 indicative that the medication container is mislabeled and communicating a notification 144 that the medication container is mislabeled.

While several embodiments have been described herein, it should be appreciated by those skilled in the art that any element or elements from one or more embodiments may be used with any other element or elements from any other embodiment or embodiments. Many modifications and other embodiments of the invention will come to the mind of one skilled in the art having the benefit of the teachings presented in the foregoing descriptions and the associated drawings. Therefore, it is understood that the invention is not to be limited to the specific embodiments disclosed, and that modifications and embodiments are intended to be included within the scope of the appended claims.

That which is claimed is:

1. A medication validation system comprising:
a mobile wireless communications device comprising a housing, wireless communications circuitry carried by the housing, and a camera carried by the housing and configured to capture an image of a medication container, the medication container having physical container characteristics associated therewith and a computer-readable indicia affixed thereon; and
a validation server configured to
obtain a plurality of stored medication physical container characteristics and associated stored computer-readable indicia,
obtain image data associated with the image from the camera, the image data representative of the physical container characteristics of the medication container,
determine the physical container characteristics of the medication container from the obtained image data,
determine the computer-readable indicia from the obtained image data,
determine whether the medication container is mislabeled based upon an attempted matching of both of the stored medication physical container characteristics and obtained physical container characteristics of the medication container and the stored computer-readable indicia and obtained computer-readable indicia indicative that the medication container is mislabeled,
communicate a notification that the medication container is mislabeled to the mobile wireless communications device for display thereat,
in response to the notification that the medication container is mislabeled, a given user being permitted to one of discard and relabel the medication container, and
apply machine learning by updating the plurality of stored medication physical container characteristics and associated stored computer-readable indicia based upon a match within respective thresholds of both of the stored medication physical container characteristics and obtained physical container characteristics of the medication container and the stored and obtained computer-readable indicia indicative that the medication container is correctly labeled.

2. The system of claim 1 comprising a medication tray comprising a plurality of partitions defining a plurality of compartments, one of the plurality of compartments for storing the medication container.

3. The system of claim 1 wherein the validation server is configured to communicate the notification to a remote device.

4. The system of claim 1 wherein the physical container characteristics comprise at least one of container shape, a container size, and a container color.

5. The system of claim 1 wherein the computer-readable indicia comprise a barcode.

6. The system of claim 1 comprising a label affixed to the medication container, the label having the computer-readable indicia printed thereon.

7. The system of claim 6 wherein the label has label text printed thereon.

8. A validation server comprising:
a processor and an associated memory configured to
obtain a plurality of stored medication physical container characteristics and associated stored computer-readable indicia,
obtain image data associated with an image of a medication container from a camera carried by a housing of a mobile wireless communications device comprising wireless communications circuitry carried by the housing, the image data representative of the physical container characteristics of the medication container, the medication container having physical container characteristics associated therewith and a computer-readable indicia affixed thereon, determine the physical container characteristics of the medication container from the obtained image data, determine the computer-readable indicia from the obtained image data, determine whether the medication container is mislabeled based upon an attempted matching of both of the stored medication physical container characteristics and obtained physical container characteristics of the medication container and the stored computer-readable indicia and obtained computer-readable indicia indicative that the medication container is mislabeled, communicate a notification that the medication container is mislabeled to the mobile wireless communications device for display thereat, in response to the notification that the medication container is mislabeled, a given user being permitted to one of discard and relabel the medication container, and apply machine learning by updating the plurality of stored medication physical container characteristics and associated stored computer-readable indicia based upon a match within respective thresholds of both of the stored medication physical container characteristics and obtained physical container characteristics of the medication container and the stored and obtained computer-readable indicia indicative that the medication container is correctly labeled.

9. The validation server of claim 8 wherein the processor is configured to communicate the notification to a remote device.

10. A method of validating a medication comprising: using a validation server to obtain a plurality of stored medication physical container characteristics and associated stored computer-readable indicia, obtain image data associated with an image of a medication container from a camera carried by a housing of a mobile wireless communications device comprising wireless communications circuitry carried by the housing, the image data representative of physical container characteristics of the medication container, the medication container having a computer-readable indicia affixed thereon, determine the physical container characteristics of the medication container from the obtained image data, determine the computer-readable indicia from the obtained image data, determine whether the medication container is mislabeled based upon an attempted matching of both of the stored medication physical container characteristics and obtained physical container characteristics of the medication container and the stored computer-readable indicia and obtained computer-readable indicia indicative that the medication container is mislabeled, communicate a notification that the medication container is mislabeled to the mobile wireless communications device for display thereat, in response to the notification that the medication container is mislabeled, a given user being permitted to one of discard and relabel the medication container, and apply machine learning by updating the plurality of stored medication physical container characteristics and associated stored computer-readable indicia based upon a match within respective thresholds of both of the stored medication physical container characteristics and obtained physical container characteristics of the medication container and the stored and determined computer-readable indicia indicative that the medication container is correctly labeled.

11. The method of claim 10 wherein using the validation server comprises using the validation server to communicate the notification to a remote device.

12. A non-transitory computer readable medium for validating a medication, the non-transitory computer readable medium comprising computer executable instructions that when executed by a processor of a validation server cause the processor to perform operations comprising:

obtaining a plurality of stored medication physical container characteristics and associated stored computer-readable indicia;

obtaining image data associated with an image of a medication container from a camera carried by a housing of a mobile wireless communications device comprising wireless communications circuitry carried by the housing, the image data representative of physical container characteristics of the medication container, the medication container having a computer-readable indicia affixed thereon;

determining the physical container characteristics of the medication container from the obtained image data;

determining the computer-readable indicia from the obtained image data;

determining whether the medication container is mislabeled based upon an attempted matching of both of the stored medication physical container characteristics and obtained physical container characteristics of the medication container and the stored computer-readable indicia and obtained computer-readable indicia indicative that the medication container is mislabeled; and communicating a notification that the medication container is mislabeled to the mobile wireless communications device for display thereat;

in response to the notification that the medication container is mislabeled, a given user being permitted to one of discard and relabel the medication container; and applying machine learning by updating the plurality of stored medication physical container characteristics and associated stored computer-readable indicia based upon a match within respective thresholds of both of the stored medication physical container characteristics and obtained physical container characteristics of the medication container and the stored and obtained computer-readable indicia indicative that the medication container is correctly labeled.

13. The non-transitory computer readable medium of claim 12 wherein the operations comprise communicating the notification to a remote device.

* * * * *